US008175371B2

(12) United States Patent
George et al.

(10) Patent No.: US 8,175,371 B2
(45) Date of Patent: May 8, 2012

(54) METHOD FOR IMAGING AND DIFFERENTIAL ANALYSIS OF CELLS

(75) Inventors: Thaddeus C. George, Seattle, WA (US); David A. Basiji, Seattle, WA (US); Brian E. Hall, Seattle, WA (US); William E. Ortyn, Bainbridge Island, WA (US); Michael E. Seo, Mercer Island, WA (US); Phillip J. Morrissey, Bellevue, WA (US); Cathleen A. Zimmerman, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 13/191,270

(22) Filed: Jul. 26, 2011

(65) Prior Publication Data

US 2011/0280467 A1    Nov. 17, 2011

Related U.S. Application Data

(63) Continuation of application No. 10/593,016, filed as application No. PCT/US2005/008870 on Mar. 16, 2005.

(60) Provisional application No. 60/553,502, filed on Mar. 16, 2004.

(51) Int. Cl.
*G06K 9/00* (2006.01)

(52) U.S. Cl. ........ 382/133; 382/128; 382/181; 382/190; 382/209; 382/224; 356/300; 356/337; 356/338; 435/4; 436/164; 436/171; 436/172; 436/63; 702/19; 702/21

(58) Field of Classification Search .................. None
See application file for complete search history.

(56) References Cited

U.S. PATENT DOCUMENTS

| 5,372,936 A * | 12/1994 | Fraatz et al. ............ 435/34 |
| 6,211,955 B1 * | 4/2001 | Basiji et al. ............ 356/326 |
| 2002/0071121 A1 * | 6/2002 | Ortyn et al. ............ 356/419 |

OTHER PUBLICATIONS

Nicoletti et al. "Common Methods for Measuring Apoptotic Cell Death by Flow Cytometry", 1997, The Purdue Cytometry CD-ROM vol. 3, Purdue University, West Lafayette.*
Young et al. "Towards automatic cell identification in DIC microscopy", Nov. 1998, Journal of Microscopy, vol. 192, Pt 2, pp. 186-193.*

* cited by examiner

*Primary Examiner* — Sath V Perungavoor
*Assistant Examiner* — Jason Heidemann
(74) *Attorney, Agent, or Firm* — Law Office of Ronald M. Anderson

(57) ABSTRACT

Provided are methods for determining and analyzing photometric and morphogenic features of small objects, such as cells to, for example, identify different cell states. In particularly, methods are provided for identifying apoptotic cells, and for distinguishing between cells undergoing apoptosis versus necrosis.

20 Claims, 8 Drawing Sheets

METHOD FOR IMAGING AND DIFFERENTIAL ANALYSIS OF CELLS

RELATED APPLICATIONS

Figure 1:
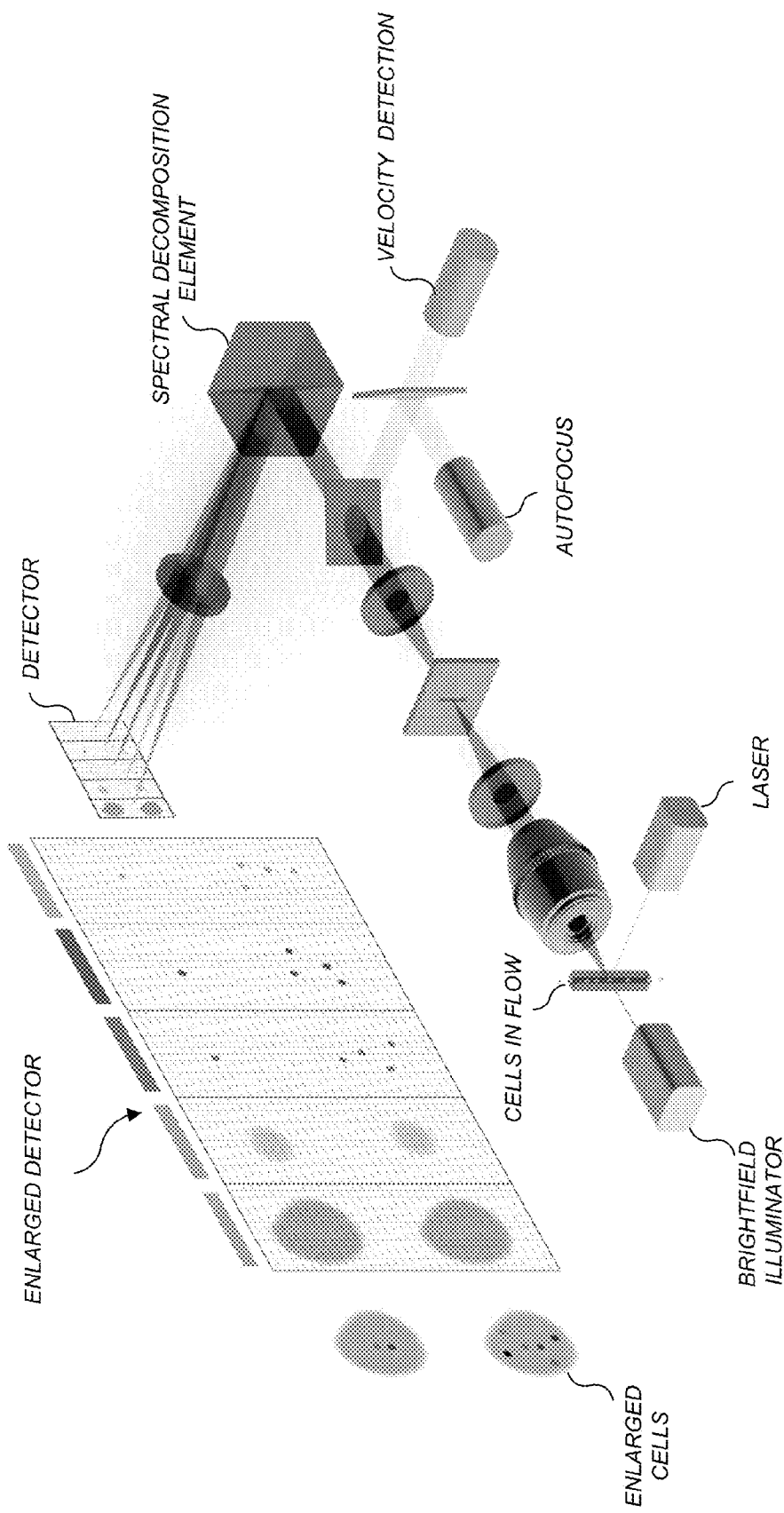

This application is a continuation of a copending patent application Ser. No. 10/593,016, filed on Sep. 14, 2006, the benefit of the filing date of which is hereby claimed under 35 U.S.C. §120. Patent application Ser. No. 10/593,016 is a National Stage application based on a prior PCT application, PCT/US05/008870, filed on Mar. 16, 2005, the benefit of the filing date of which is hereby claimed under 35 U.S.C. §371. PCT/US05/008870 itself is based on a prior provisional application Ser. No. 60/553,502, filed on Mar. 16, 2004, the benefit of the filing date of which is hereby claimed under 35 U.S.C. §119(e).

BACKGROUND

Apoptosis is a complex, tightly regulated process by which a cell orchestrates its own destruction in response to specific internal or external triggers (Jacobson et al., Cell 88:347, 1997; Rathmell and Thompson, Cell 109 (Supp):S97, 2002), and proceeds in a manner that is designed to prevent damage to surrounding cells and tissues. Apoptotic cells typically appear shrunken, with condensed chromatin and fragmented nuclei. Although plasma membrane integrity is initially preserved, in later stages the plasma membrane becomes compromised and the cells shed apoptotic bodies consisting of organelles, cytoplasm and/or nuclear fragments. Apoptotic cells are rapidly phagocytosed and eliminated in vivo, thus preventing the induction of inflammatory responses, which is a process critical to the maintenance of tissue and immune cell development and homeostasis (Jacobson et al.; Rathmell and Thompson; Vaux and Korsmeyer, Cell 96:245, 1999). Inappropriately low apoptotic rates can result in cancer or autoimmune disease, while high rates can result in neurodegenerative disease or immunodeficiency (Ashkenazi and Dixit, Science 281:1305, 1998; Thompson, Science 267:1456, 1995; Fadeel et al., Leukemia 14:1514, 2000). In contrast, necrotic cell death is a largely unregulated process in which the cells generally have intact nuclei with limited chromatin condensation. Cells undergoing necrosis do not induce an early phagocytic response. Instead, the cells swell and rupture, and the release of cellular contents can result in significant local tissue damage and inflammation (Jacobson et al.).

Research aimed at cell death regulation has produced a number of methods to identify and quantify apoptotic cells, and to distinguish between cells undergoing apoptosis versus necrosis. Among these, flow cytometry has become a commonly used tool in the identification and quantification of apoptosis. Changes in cell size, shape, and granularity associated with apoptosis can be inferred from scattered laser light (Ormerod et al., J. Immunol. Methods 153:57, 1992). Early intracellular events, such as the loss of the mitochondrial inner membrane potential or activation and cleavage of caspases, can also be detected using electro-potential sensitive dyes (Castedo et al., J. Immunol. Methods 265:39, 2002; Green and Kroemer, Trends Cell. Biol. 8:267, 1998; Green and Reed, Science 281:1309, 1998; Kroemer and Reed, Nat. Med. 6:513, 2000; Lizard et al., Cytometry 21:275, 1995) or fluorogenic substrates (Komoriya et al., J. Exp. Med. 191:1819, 2000; Smolewski et al., J. Immunol. Methods 265:111, 2002; Lecoeur et al., J. Immunol. Methods 265:81, 2002). Another early apoptotic event results in exposure of phosphatidylserine on the outer surface of the plasma membrane, which can be detected by fluorochrome-labeled annexin V (van Engeland et al., Cytometry 31:1, 1998; Vermes et al., J. Immunol. Methods 184:39, 1995; Koopman et al., Blood 84:1415, 1994; Verhoven et al., J. Exp. Med. 182:1597, 1995). Apoptotic cells eventually lose the ability to exclude cationic nucleotide-binding dyes and nuclear DNA stains with dyes, such as propidium iodide and 7-aminoactinomycin D (7-AAD) (Lecoeur et al., 2002; Gaforio et al., Cytometry 49:8, 2002; Ormerod et al., Cytometry 14:595, 1993; Schmid et al., J. Immunol. Methods 170:145, 1994; Philpott et al., Blood 87:2244, 1996). Other techniques that can be used to identity apoptosis include biochemical identification of the activated proteases (e.g., caspases, PARP), release of mitochondrial cytochrome c, quantification of cellular DNA content, and progressive endonucleolytic cleavage of nuclear DNA (Alnemri et al., Cell 87:171, 1996; Kohler et al., J. Immunol. Methods 265:97, 2002; Gong et al., Anal. Biochem. 218:314, 1994; Gorczyca et al., Leukemia 7:659, 1993; Gorczyca et al., Cancer Res. 53:1945, 1993).

As noted above, conventional flow cytometric methods do not provide direct morphologic evidence of cell death. Indeed, these techniques usually target molecular changes that are associated with apoptosis, but such changes are not always specific to apoptosis and may also be present in cells undergoing necrotic death (Lecoeur et al., 2002; Lecoeur et al., Cytometry 44:65, 2001; Kerr et al., Br. J. Cancer 26:239, 1972). For example, necrotic cells, like advanced (late-stage) apoptotic cells, stain with both annexin V and 7-AAD (Lecoeur et al., 2002; Lecoeur et al., 2001). Thus, visualization of the characteristic morphologic changes associated with apoptosis is still considered to be absolutely necessary for its identification (Jacobson et al.; Darzynkiewicz et al. Cytometry 27:1, 1997). Standard microscopic techniques allow visualization of specific molecular and biochemical changes associated with apoptosis and also morphologic changes that distinguish apoptosis from necrosis. However, these standard techniques also require subjective analysis and time-consuming image viewing, which only allows for processing of relatively limited numbers of cells and, therefore, makes it difficult to attain statistically valid comparisons (Tarnok and Gerstner, Cytometry 50:133, 2002).

Thus, the need exists for techniques that can provide the statistical power offered by flow cytometry coupled with the objective assessment capabilities associated with microscopic analysis. For example, interest in the dynamic nature of the living cell and efforts to model cell processes (variously termed "cytomics" or "systems biology") are powerful drivers for new techniques to acquire ever more comprehensive data from cells and cell populations. The present invention meets such needs, and further provides other related advantages.

SUMMARY

This application specifically incorporates by reference the disclosures and drawings of each patent application and issued patent identified above as a related application.

The concepts disclosed herein encompass a method for classifying a specific cell as one of the following four types of cells, a viable cell, a necrotic cell, an early apoptotic cell (in which a cellular membrane of the cell is still intact), and a late apoptotic cell (in which the cellular membrane of the cell is not intact), using only a single nuclear marker and image data from the cell. An exemplary such method includes the steps of: (a) exposing the specific cell to only a single nuclear marker that will bind to DNA in a nucleus of the specific cell in the event that the cellular membrane of the specific cell is not intact; (b) collecting image data from the specific cell, the image data including a darkfield image (i.e., a side scatter image of the specific cell), a brightfield image of the specific cell, and a fluorescent image of the specific cell (the fluorescent image enabling the location of the single nuclear marker in the specific cell to be determined); (c) using the brightfield image of the specific cell and the fluorescent image of the specific cell to calculate a cytoplasmic size of the specific cell; (d) analyzing the fluorescent image of the specific cell to determine if the nuclear marker is present in the nucleus of the specific cell; (e) using the darkfield image of the specific cell to calculate a spatial scatter frequency metric indicative of a granularity of the specific cell; and (f) classifying the specific cell as one of the four types of cells based on the cytoplasmic size of the specific cell, the darkfield scatter frequency metric of the specific cell, and the presence (or absence) of the nuclear marker in the nucleus of the specific cell.

At least one related method includes the step of classifying the specific cell as a viable cell when: (a) the cytoplasmic size of the specific cell is larger than a cytoplasmic size of a cell known to be an early apoptotic cell in which a cellular membrane of the cell is still intact; (b) the darkfield scatter frequency metric of the specific cell is smaller than a darkfield scatter frequency metric of a cell known to be an early apoptotic cell in which a cellular membrane of the cell is still intact; and (c) the nuclear marker is not present in the nucleus of the specific cell.

At least one related method includes the step of classifying the specific cell as a viable cell when: (a) the cytoplasmic size of the specific cell is larger than a cytoplasmic size of a cell known to be an early apoptotic cell in which a cellular membrane of the cell is still intact; and (b) the nuclear marker is not present in the nucleus of the specific cell.

At least one related method includes the step of classifying the specific cell as a viable cell when: (a) the darkfield scatter frequency metric of the specific cell is smaller than a darkfield scatter frequency metric of a cell known to be an early apoptotic cell in which a cellular membrane of the cell is still intact; and (b) the nuclear marker is not present in the nucleus of the specific cell.

At least one related method includes the step of classifying the specific cell as an early apoptotic cell in which a cellular membrane of the cell is still intact when: (a) the cytoplasmic size of the specific cell is smaller than a cytoplasmic size of a cell known to be a viable cell in which a cellular membrane of the cell is still intact; (b) the darkfield scatter frequency metric of the specific cell is larger than a darkfield scatter frequency metric of a cell known to be a viable cell in which a cellular membrane of the cell is still intact; and (c) the nuclear marker is not present in the nucleus of the specific cell.

At least one related method includes the step of classifying the specific cell as an early apoptotic cell in which a cellular membrane of the cell is still intact when: (a) the cytoplasmic size of the specific cell is smaller than a cytoplasmic size of a cell known to be a viable cell in which a cellular membrane of the cell is still intact; and (b) the nuclear marker is not present in the nucleus of the specific cell.

At least one related method includes the step of classifying the specific cell as a late apoptotic cell in which a cellular membrane of the cell is not intact when: (a) the darkfield scatter frequency metric of the specific cell is larger than a darkfield scatter frequency metric of a cell known to be a necrotic cell; and (b) the nuclear marker is present in the nucleus of the specific cell.

At least one related method includes the step of classifying the specific cell as a necrotic cell when: (a) the darkfield scatter frequency metric of the specific cell is smaller than a darkfield scatter frequency metric of a cell known to be a late apoptotic cell; and (b) the nuclear marker is present in the nucleus of the specific cell.

In yet another related method, the single nuclear marker is 7-aminoactinomycin D.

Still another aspect of the concepts disclosed herein is a method for classifying a specific cell as one of the following four types of cells, a viable cell, a necrotic cell, an early apoptotic cell (in which a cellular membrane of the cell is still intact), and a late apoptotic cell (in which the cellular membrane of the cell is not intact), using only a single nuclear marker and image data from the cell, using a slightly different series of steps. An exemplary such method includes the steps of: (a) exposing the specific cell to only a single nuclear marker that will bind to DNA in a nucleus of the specific cell in the event that the cellular membrane of the specific cell is not intact; (b) collecting image data from the specific cell, the image data including a darkfield image (i.e., side scatter image) of the specific cell, and a fluorescent image of the specific cell (the fluorescent image enabling the location of the single nuclear marker in the specific cell to be determined); (c) analyzing the fluorescent image of the specific cell to determine if the nuclear marker is present in the nucleus of the specific cell; (d) using the darkfield image of the specific cell to calculate a spatial scatter frequency metric indicative of a granularity of the specific cell; (e) classifying the specific cell as being a viable cell when the nuclear marker is not present in the nucleus of the specific cell and the darkfield scatter frequency metric of the specific cell is smaller than a darkfield scatter frequency metric of a cell known to be an early apoptotic cell in which a cellular membrane of the cell is still intact; (f) classifying the specific cell as being an early apoptotic cell when the nuclear marker is not present in the nucleus of the specific cell and the darkfield scatter frequency metric of the specific cell is larger than a darkfield scatter frequency metric of a cell known to be a viable cell; (g) classifying the specific cell as being a late apoptotic cell when the nuclear marker is present in the nucleus of the specific cell and the darkfield scatter frequency metric of the specific cell is larger than a darkfield scatter frequency metric of a cell known to be a necrotic cell; and (h) classifying the specific cell as being a necrotic cell when the nuclear marker is present in the nucleus of the specific cell and the darkfield scatter frequency metric of the specific cell is smaller than a darkfield scatter frequency metric of a cell known to be a late apoptotic cell.

In at least one related method, the single nuclear marker is 7-aminoactinomycin D.

Still another aspect of the concepts disclosed herein is related to yet another method for classifying a population of biological cells into four different types of cells, the four types of cells consisting of viable cells, necrotic cells, early apoptotic cells (in which a cellular membrane of the cell is still intact), and late apoptotic cells (in which the cellular membrane of the cell is not intact), using only a single nuclear marker and image data acquired from each cell in the population of cells. An exemplary such method includes the steps of: (a) exposing each cell in the population of cells to only one nuclear marker that will bind to DNA in a nucleus of the cell in the event that the cellular membrane of the cell is not intact; (b) collecting image data from the specific cell, the image data including a darkfield image (i.e., a side scatter image of the specific cell), a brightfield image of the specific cell, and a fluorescent image of the specific cell (the fluorescent image enabling the location of the single nuclear marker in the specific cell to be determined); (c) for each specific cell in the population of cells, using the brightfield image of the specific cell and the fluorescent image of the specific cell to calculate a cytoplasmic size of the specific cell; (d) for each specific cell in the population of cells, using the darkfield image of the specific cell to calculate a spatial scatter frequency metric indicative of a granularity of the specific cell; (e) generating a dot plot where data from each cell in the population of cells is displayed, the dot plot being generated using the cytoplasmic size of each cell as a first axis of the dot plot, and the spatial scatter frequency metric of the darkfield image of each cell as a second axis of the dot plot; and (f) using the dot plot to classify the population of cells into the four different types of cells based on the relative location of each cell in the dot.

At least one related method includes the step of displaying each viable cell on the dot plot at a first portion of the dot plot corresponding to cells having a relatively larger cytoplasmic size and a relatively lower darkfield scatter frequency metric. In an exemplary dot plot, the first portion of the dot plot corresponds to a lower left quadrant of the dot plot.

At least one related method includes the step of displaying each early apoptotic cell on the dot plot at a second portion of the dot plot corresponding to cells having a relatively larger cytoplasmic size and a relatively higher darkfield scatter frequency metric. In an exemplary dot plot, the second portion of the dot plot corresponds to an upper left quadrant of the dot plot.

At least one related method includes the step of displaying each necrotic cell on the dot plot at a third portion of the dot plot corresponding to cells having a relatively smaller cytoplasmic size and a relatively lower darkfield scatter frequency metric. In an exemplary dot plot, the third portion of the dot plot corresponds to a lower right quadrant of the dot plot.

At least one related method includes the step of displaying each late apoptotic cell on the dot plot at a fourth portion of the dot plot corresponding to cells having a relatively smaller cytoplasmic size and a relatively higher darkfield scatter frequency metric. In an exemplary dot plot, the, fourth portion of the dot plot corresponds to an upper right quadrant of the dot plot.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 shows a schematic representation of the ImageStream 100™ multispectral imaging cytometer.

Figure 2A:
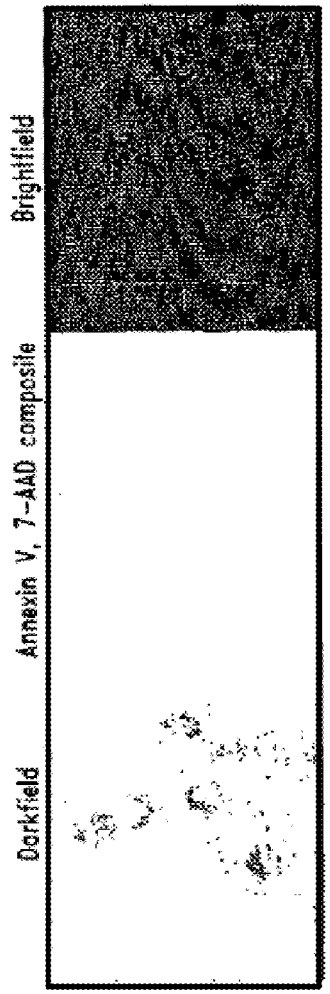
Figure 2B:
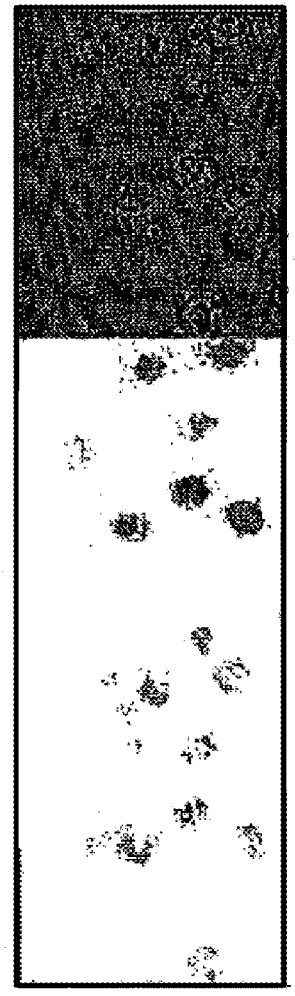
Figure 2C:
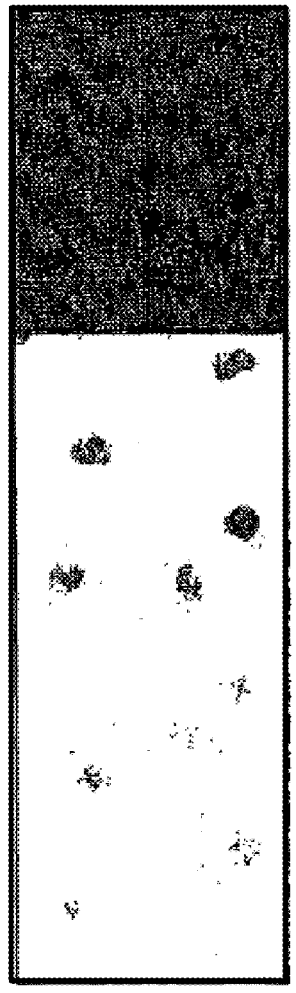

FIGS. 2A-2C show an analysis of cell death using standard flow cytometry and immunofluorescence microscopy. Untreated Jurkat cells (A), Jurkat cells treated with 1 .mu.M CPT for 18 hrs (B), and Jurkat cells treated with 0.3% hydrogen peroxide for 1 hour (C) were stained with Alexa Fluor 488 conjugated annexin V and 7-AAD. Cells were analyzed either by conventional flow cytometry (using a BD FACSort™) or visualized on slides using a Nikon Eclipse E600 fluorescence microscope equipped with bandpass filters appropriate for Alexa Fluor 488 (535/40 nm) and 7-AAD (630/60 nm) fluorescence. The 2-color dot-plots of annexin V vs. 7-AAD, and the brightfield, combined fluorescence and darkfield microscopic images are shown.

FIGS. 3A-3E show flow cytometric imaging of untreated, CPT-treated and peroxide-treated Jurkat cells that were stained with Alexa Fluor 488 conjugated annexin V and 7-AAD. Peroxide-treated cells were also separately stained with HLA class I-PE. After staining, equal cell numbers of the three populations of cells were mixed and analyzed by (A) conventional flow cytometry using a FACSort™; and (B) multispectral imaging of cells in flow using the ImageStream 100™ cytometer. The six channel images of cells from representative members of the double positive (DP), single positive (SP), and double negative (DN) populations identified using the ImageStream 100™ are shown in panels C, D and E, respectively.

Figure 3A:
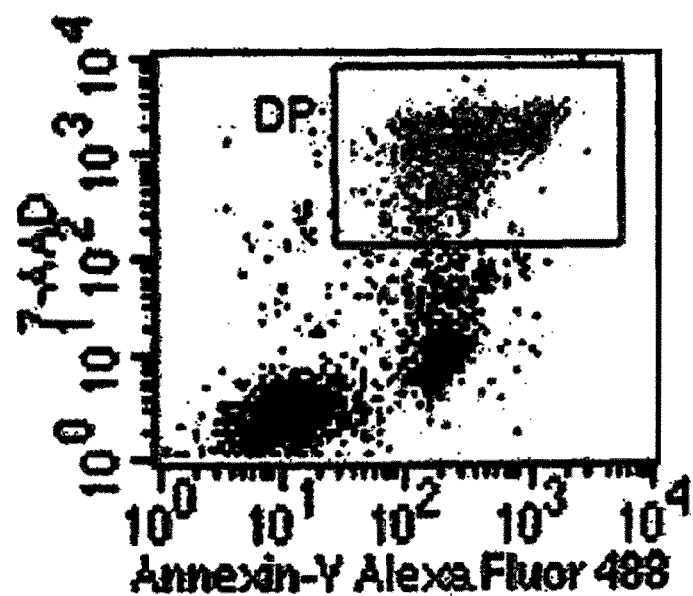

FIGS. 4A-4F show (A) a laser scatter analysis (forward scatter vs. side scatter) of the "DP gate" population of cells from FIG. 3A, by way of CellQuest™ software on data obtained from a FACSort™ cytometer; (B) a single color histogram of HLA class I-PE on DP cells from FIG. 3A as measured using a FACSort™. cytometer; (C) backgating of HLA class I-PE.sup.+ cells from FIG. 4B onto the scatter histogram of FIG. 4A, wherein HLA class I-PE.sup.+ cells (i.e., peroxide-treated, necrotic) are shown in red and HLA class I-PE.sup.− cells (i.e., CPT-treated, apoptotic) are shown in blue; (D) a bivariate plot (scatter histogram) of the "Brightfield Area" vs. the "488 nm Scatter Peak Intensity" produced using IDEAS™ software on data obtained using the ImageStream 100™ cytometer; (E) a single color histogram of HLA class I-PE on DP cells from FIG. 3D as measured using the ImageStream 100™ cytometer; (F) backgating of HLA class I-PE.sup.+ cells from FIG. 4E onto the scatter histogram of FIG. 4D, wherein HLA class I-PE.sup.+ cells (i.e., peroxide-treated, necrotic) are shown in red and HLA class I-PE.sup.− cells (i.e., CPT-treated, apoptotic) are shown in yellow.

Figure 4A:
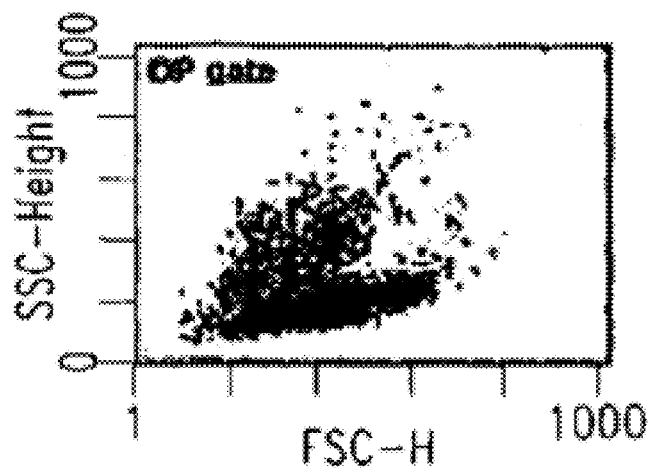
Figure 4B:
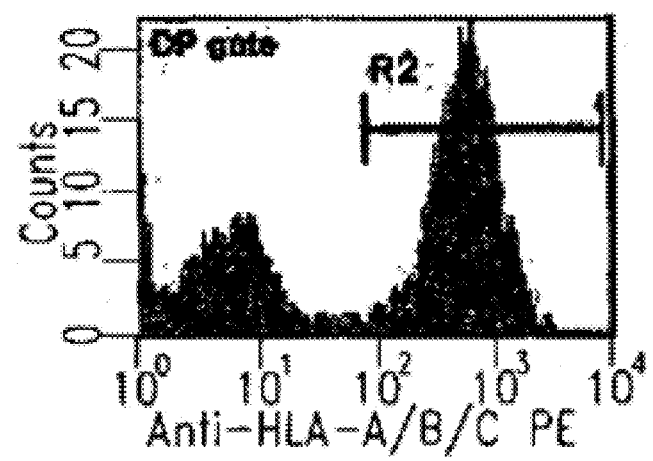
Figure 4C:
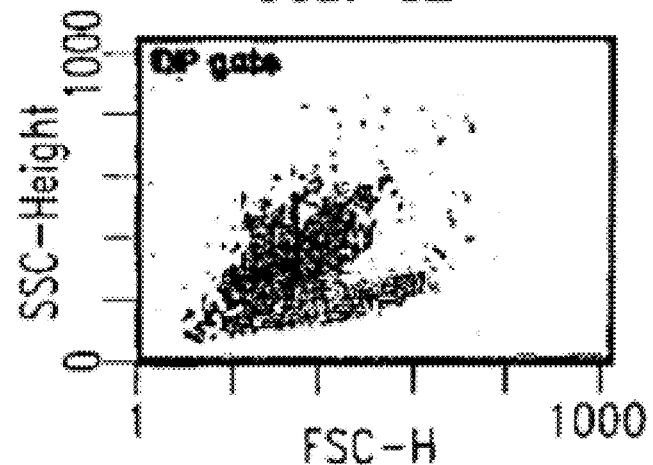
Figure 4D:
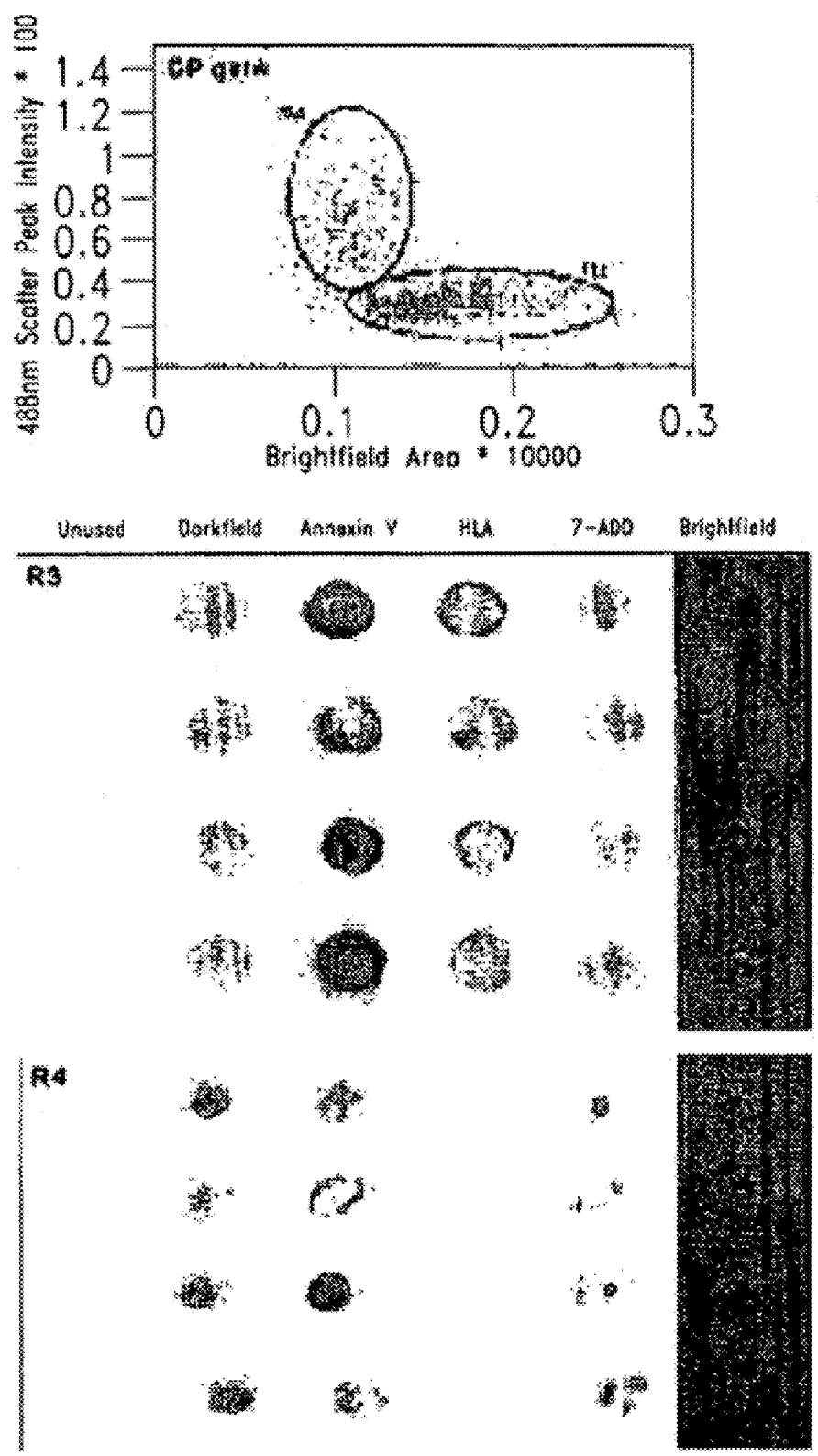
Figure 4E:
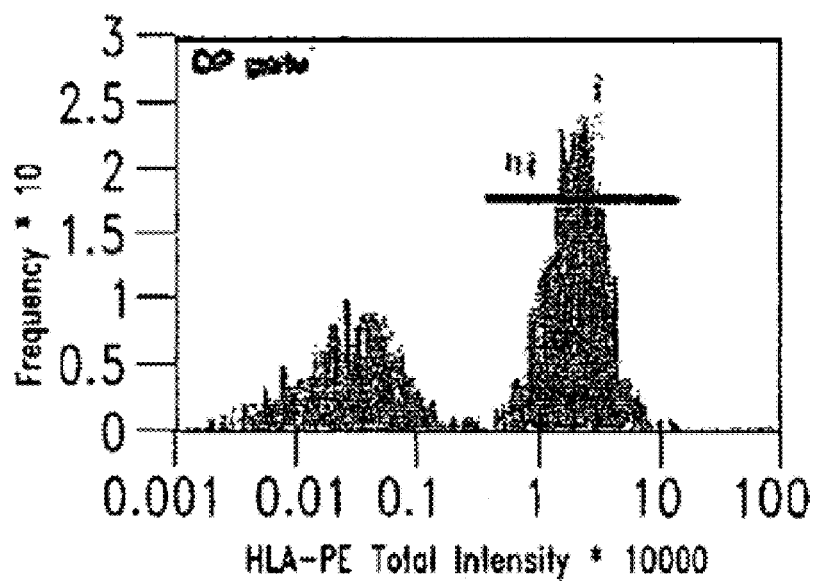
Figure 4F:
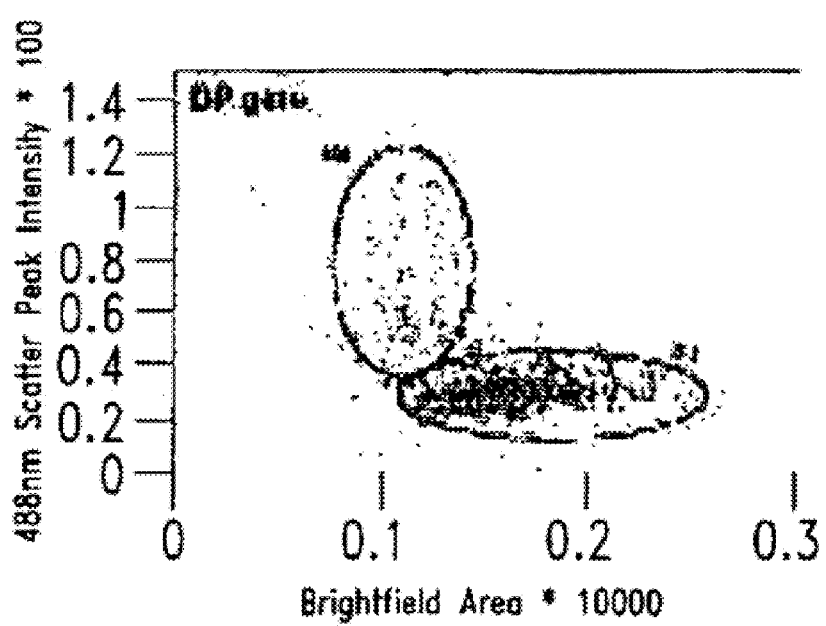
Figure 5:
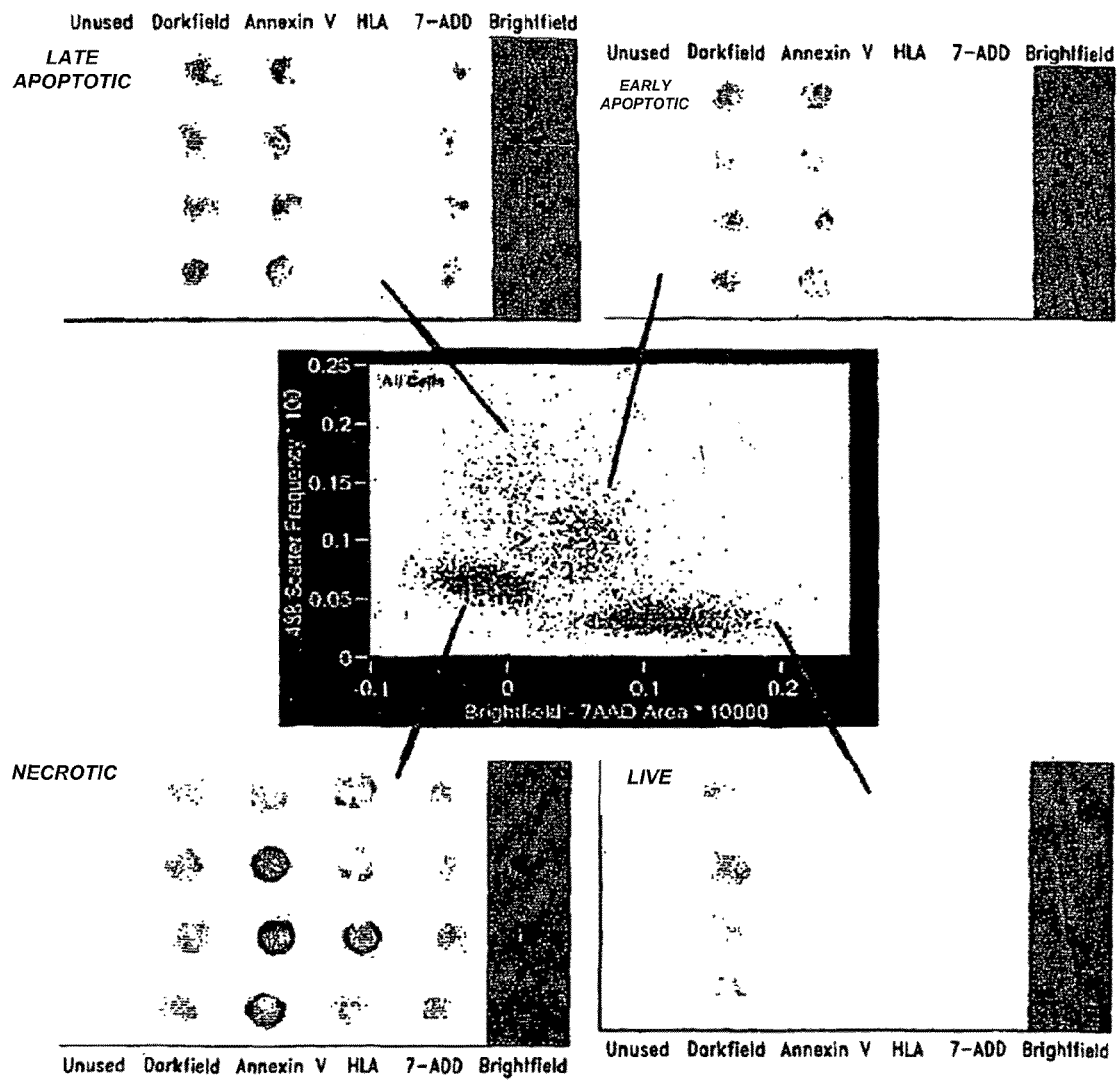

FIG. 5 shows resolution of live, early and late apoptotic, and necrotic cells using morphometric features based on scatter intensity, brightfield area, and nuclear area. Backgating of the four cell populations that had been identified using alternative criteria confirmed their identity as live cells and early apoptotic cells with the DN and SP cells, respectively, shown in FIG. 3B (shown in blue and green, center panel), and as necrotic and late apoptotic cells with cells contained in gates R3 and R4, respectively, shown in FIG. 4 (shown in yellow and red, center panel). Note that color Figures have not been provided, however, the different cell populations (live, early apoptotic, late apoptotic, and necrotic) are displayed in different colors in the IDEAS™ software.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

The instant disclosure relates to the use of both photometric and morphometric features derived from multi-mode imagery of objects (e.g., cells) in flow to discriminate cell states or types, and cell features, in heterogeneous populations of cells, including both non-adherent and adherent cell types. A surprising result of the instant disclosure is the ability to discriminate between different cell states, such as differentiating and identifying live cells, necrotic cells, and cells in both the early and late stages of apoptosis, by using unique combinations of features provided in the ImageStream 100™ Multispectral Imaging Cytometer and the IDEAS™ data analysis software. Discussed in more detail below are single-step methods for basic and complex morphometric classification of objects in flow, which may be combined with comprehensive multispectral imagery and photometric features to allow, for example, the identification of different cell features and/or cell types or states not feasible with standard flow cytometry.

In the present description, any concentration range, percentage range, or integer range is to be understood to include the value of any integer within the recited range and, when appropriate, fractions thereof (such as one tenth and one hundredth of an integer, etc.), unless otherwise indicated. As used herein, the term "about" means plus or minus 15%. As used herein, the use of an indefinite article, such as "a" or "an", should be understood to refer to the singular and the plural of a noun or noun phrase (i.e., meaning "one or more" of the enumerated elements or components). The use of the alternative (e.g., "or") should be understood to mean either one, both or any combination thereof of the alternatives.

By way of background, methodologies for simultaneous high speed multispectral imaging in brightfield, darkfield, and four channels of fluorescence of cells in flow were recently developed (see, e.g., U.S. Pat. Nos. 6,211,955 and 6,249,341). FIG. 1 illustrates an exemplary imaging system (e.g., the ImageStream platform). Cells are hydrodynamically focused into a core stream and orthogonally illuminated for both darkfield and fluorescence imaging. The cells are simultaneously trans-illuminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is 0.5 microns square, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object.

Prior to projection on the CCD, the light is passed through a spectral decomposition optical system that directs different spectral bands to different lateral positions across the detector (see, e.g., U.S. Pat. No. 6,249,341). With this technique, an image is optically decomposed into a set of 6 sub-images, each corresponding to a different color component and spatially isolated from the remaining sub-images. This process allows for identification and quantitation of signals within the cell by physically separating on the detector signals that may originate from overlapping regions of the cell. Spectral decomposition also allows multimode imaging: the simultaneous detection of brightfield, darkfield, and multiple colors of fluorescence. This is exemplified in FIG. 1, which depicts a red brightfield illumination source and the associated transmitted light images in the red detector channel adjacent to fluorescent and scattered light images in the other spectral channels. The process of spectral decomposition occurs during the image formation process rather than via digital image processing of a conventional composite image.

The CCD may be operated using a technique called time-delay-integration (TDI), a specialized detector readout mode that preserves sensitivity and image quality even with fast relative movement between the detector and the objects being imaged. As with any CCD, image photons are converted to photocharges in an array of pixels. However, in TDI operation, the photocharges are continuously shifted from pixel to pixel down the detector, parallel to the axis of flow. If the photocharge shift rate is synchronized with the velocity of the flowing cell's image, the effect is similar to physically panning a camera: image streaking is avoided despite signal integration times that are orders of magnitude longer than in conventional flow cytometry. For example, an instrument may operate at a continuous data rate of approximately 30 megapixels per second and integrate signals from each object for 10 milliseconds, allowing the detection of even faint fluorescent probes within cell images that are acquired at high-speed. Careful attention to pump and fluidic system design to achieve highly laminar, non-pulsatile flow eliminates any cell rotation or lateral translation on the time scale of the imaging process (see, e.g., U.S. Pat. No. 6,532,061).

A real-time algorithm analyzes every pixel read from the CCD to detect the presence of object images and calculate a number of basic morphometric and photometric features, which can be used as criteria for data storage. Data files encompassing 10,000-20,000 cells are typically about 100 MB in size and, therefore, can be stored and analyzed using standard personal computers. The TDI readout process operates continuously without any "dead time", which means every cell can be imaged and the coincidental imaging of two or more cells at a time, as depicted in FIG. 1, presents no barrier to data acquisition.

Such an imaging system can be employed to determine morphological, photometric, and spectral characteristics of cells and other objects by measuring optical signals, including light scatter, reflection, absorption, fluorescence, phosphorescence, luminescence, etc. As used herein, morphological parameters may be basic (e.g., nuclear shape) or may be complex (e.g., identifying cytoplasm size as the difference between cell size and nuclear size). For example, morphological parameters may include nuclear area, perimeter, texture or spatial frequency content, centroid position, shape (i.e., round, elliptical, barbell-shaped, etc.), volume, and ratios of any of these parameters. Morphological parameters may also include cytoplasm size, texture or spatial frequency content, volume and the like, of cells. As used herein, photometric measurements with the aforementioned imaging system can enable the determination of nuclear optical density, cytoplasm optical density, background optical density, and the ratios of any of these values. An object being imaged can be stimulated into fluorescence or phosphorescence to emit light, or may be luminescent wherein light is produced without stimulation. In each case, the light from the object may be imaged on a TDI detector of the imaging system to determine the presence and amplitude of the emitted light, the number of discrete positions in a cell or other object from which the light signal(s) originate(s), the relative placement of the signal sources, and the color (wavelength or waveband) of the light emitted at each position in the object.

The present disclosure provides methods of using both photometric and morphometric features derived from multi-mode imagery of objects in flow. Such methods can be employed as a cell analyzer to determine one or more cell states or types, and cell features, in heterogeneous populations of cells when entrained in a fluid flowing through an imaging system. As used herein, cell states or types may include live cells, cells early or late in the process of dying (e.g., apoptotic cells or necrotic cells), cells propagating (e.g., cells in different phases of division), populations and subpopulations of cells (e.g., leucocyte subpopulations in blood), etc., and combinations thereof. However, it should also be understood that these exemplary methods might be used for imaging and distinguishing other moving objects that have identifiable photometric and morphometric features. As used herein, gating refers to a subset of data relating to photometric or morphometric imaging. For example, a gate may be a numerical or graphical boundary of a subset of data that can be used to define the characteristics of particles to be further analyzed. Here, gates have been defined, for example, as a plot boundary that encompasses viable (normal) cells as double negatives (DN gate), or early apoptotic cells as single positives (SP gate), or late apoptotic and necrotic cells as double positives (DP gate). Further, backgating may be a subset of the subset data. For example, a forward scatter versus a side scatter plot in combination with a histogram from an additional marker (e.g., HLA-class I-PE) may be used to backgate a subset (e.g., late apoptotic cells) within the initial subset (e.g., late apoptotic and necrotic cells).

In using an imaging system as described herein, it should be made clear that a separate light source is not required to produce an image of the object (cell), if the object is luminescent (i.e., if the object produces light). However, many of the applications of an imaging system as described herein will require that one or more light sources be used to provide light that is incident on the object being imaged. A person having ordinary skill in the art will know that the location of the light sources substantially affects the interaction of the incident light with the object and the kind of information that can be obtained from the images on a TDI detector.

In addition to imaging an object with the light that is incident on it, a light source can also be used to stimulate emission of light from the object. For example, a cell having been contacted with probe conjugated to a fluorochrome (e.g., such as FITC, PE, APC, Cy5, or Cy5.5) will fluoresce when excited by light, producing a corresponding characteristic emission spectra from any excited fluorochrome probe that can be imaged on a TDI detector. Light sources may alternatively be used for causing the excitation of fluorochrome probes on an object, enabling a TDI detector to image fluorescent spots produced by the probes on the TDI detector at different locations as a result of the spectral dispersion of the light from the object that is provided by prism. The disposition of these fluorescent spots on the TDI detector surface will depend upon their emission spectra and their location in the object.

Each light source may produce light that can either be coherent, non-coherent, broadband or narrowband light, depending upon the application of the imaging system desired. Thus, a tungsten filament light source can be used for applications in which a narrowband light source is not required. For applications such as stimulating the emission of fluorescence from probes, narrowband laser light is preferred, since it also enables a spectrally decomposed, non-distorted image of the object to be produced from light scattered by the object. This scattered light image will be separately resolved from the fluorescent spots produced on a TDI detector, so long as the emission spectra of any of the spots are at different wavelengths than the wavelength of the laser light. The light source can be either of the continuous wave (CW) or pulsed type, preferably a pulsed laser. If a pulsed type illumination source is employed, the extended integration period associated with TDI detection can allow the integration of signal from multiple pulses. Furthermore, it is not necessary for the light to be pulsed in synchronization with the TDI detector.

In the embodiments of the present invention, it is to be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion, which movement may be in different directions and/or at different rates.

In certain aspects, there is provided a method for identifying a specific cell, comprising directing incident light at a cell, using a detector to obtain a side scatter image, and using the spatial frequency content of the side scatter image to identify a specific cell. Within certain embodiments, the methods of the instant disclosure may be used to identify a specific cell subpopulation that is part of larger heterogeneous cell population. For example, the methods of this disclosure may be used to identify a normal cell, a cell undergoing apoptosis (including early and late stage apoptosis), and a cell undergoing necrosis. Alternatively, the methods of the instant disclosure may be used to identify cells at particular stages of replication (S phase, G phase, M phase, etc.). Thus, in a heterogeneous population of cells, the methods of the invention may be used to identify at least one apoptotic cell and at least one necrotic cell and at least one normal (viable) cell. In addition, early stage and late stage apoptotic cells may be indentified.

In another aspect, the instant disclosure provides a method for identifying a specific cell, comprising directing incident light at a cell, using a detector to obtain a brightfield image, and using the spatial frequency content of the brightfield image to identify a specific cell. In certain embodiments, the spatial frequency content analyzed is of the nucleus. Any of the aforementioned embodiments may be used within the context of this aspect of the invention.

In a further aspect, the instant disclosure provides a method for identifying a specific cell, comprising contacting a cell with a nuclear marker, directing incident light at the marked cell, using a detector to obtain an image of the cell, and using the nuclear marker image in combination with the spatial frequency content of the cell image to identify a specific cell. Again, any of the previous embodiments may be used within this method. In certain embodiments, only a single nuclear marker is used, such as 7-AAD.

In any of the aforementioned methods, multiple images may be collected simultaneously. Furthermore, in any of the aforementioned methods, there is relative motion between the cell and the detector. In addition, in any of the aforementioned methods, the detector is a time delay integration charge-coupled detector.

The instant disclosure also provides a kit for use in a multispectral imaging system to identify a specific cell type, comprising a single nuclear marker, wherein a cell contacted with the single marker for a time sufficient to allow identification of an apoptotic cell or a necrotic cell with the multispectral imaging system, as described herein.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. The invention having been described, the following examples are intended to illustrate, and not limit, the invention.

EXAMPLES

Example 1

Induction of Apoptosis

Human acute T leukemic Jurkat cell line was obtained from ATCC (Rockville, Md.; catalog number CRL-1990) and maintained in RPMI 1640 (Gibco, Grand Island, N.Y.) containing 5% fetal bovine serum, 1 mM sodium pyruvate (Mediatech, Herndon, Va.), 100 .mu.M nonessential amino acids, 100 U/ml penicillin, 100 .mu.g/ml streptomycin, and 2 mM L-glutamine (BioWhittaker, Walkersville, Md.) in 5% CO.sub.2 atmosphere at 37 degrees C. The density of exponentially growing cells was less than 3.times.10.sup.5 cells per ml at the time of all treatments. To induce apoptosis, cells were treated for 18 hours with 1 .mu.M camptothecin (CPT, Sigma), a DNA topoisomerase I inhibitor.

Example 2

Induction of Necrosis

Human acute T leukemic Jurkat cell line was obtained from ATCC (Rockville, Md.; catalog number CRL-1990) and maintained in RPMI 1640 (Gibco, Grand Island, N.Y.) containing 5% fetal bovine serum, 1 mM sodium pyruvate (Mediatech, Herndon, Va.), 100 .mu.M nonessential amino acids, 100 U/ml penicillin, 100 .mu.g/ml streptomycin, and 2 mM L-glutamine (BioWhittaker, Walkersville, Md.) in 5% CO.sub.2 atmosphere at 37.degree. C. The density of exponentially growing cells was less than 3.times.10.sup.5 cells per ml at the time of all treatments. To induce necrosis, cells were treated for 1 hour with 0.3% hydrogen peroxide (Sigma, St. Louis, Mo.).

Example 3

Staining to Identify Apoptotic Cells and Necrotic Cells

Control (untreated) cell, CPT treated (apoptotic) cells, and peroxide treated (necrotic) cells were independently counted and washed once in phosphate buffered saline (PBS, Fair Lawn, N.J.). Each cell group was resuspended at 10.sup.7 cells/ml in annexin V Binding Buffer (BD Pharmingen, San Diego, Calif.) containing Alexa Fluor 488 annexin V (Molecular Probes, Eugene, Oreg.) and 10 .mu.M 7-aminoactinomycin D (7-AAD, Molecular Probes) for 10 minutes at room temperature. Necrotic cells were additionally stained with phycoerythrin (PE)-labeled anti-HLA-A, B, C (clone G46-2.6, BD Pharmingen; anti-HLA class I). Each cell group was washed in annexin V Binding Buffer, fixed in 2% paraformaldehyde (Sigma), and analyzed as either single populations or as a mixture by flow cytometry and immunofluorescence microscopy.

Example 4

Conventional Flow Cytometry and Imaging Flow Cytometry

For flow cytometry, cell fluorescence data excited by a 488 nm laser were acquired using the FACSort™ cytometer (BD Immunocytometry Systems, San Jose, Calif.) and analyzed using CellQuest™ (BD Immunocytometry Systems). For imaging flow cytometry, fixed cells at 5.times.10.sup.7 cells per ml were run at 100 cells per second on an ImageStream 100™ ("Beta" version), and the data analyzed using the ImageStream Data Analysis and Exploration Software (IDEAS™).

Example 5

Instrumentation for Multispectral Imaging Flow Cytometry

FIG. 1 provides an exemplary layout of the ImageStream 100™ platform. Cells are hydrodynamically focused into a core stream and orthogonally illuminated for both darkfield and fluorescence imaging. The cells are simultaneously transilluminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is 0.5 microns square, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object.

Prior to projection on the CCD, the light is passed through a spectral decomposition optical system that directs different spectral bands to different lateral positions across the detector (see, e.g., U.S. Pat. No. 6,249,341). With this technique, an image is optically decomposed into a set of 6 sub-images, each corresponding to a different color component and spatially isolated from the remaining sub-images. This is exemplified in FIG. 1, which depicts a red brightfield illumination source and the associated transmitted light images in the red detector channel adjacent to fluorescent and scattered light images in the other spectral channels. The process of spectral decomposition occurs during the image formation process rather than via digital image processing of a conventional composite image.

The CCD is operated using time-delay-integration (TDI), in which image photons converted to photocharges in an array of pixels are continuously shifted (at a rate synchronized with the velocity of the flowing cell's image) from pixel to pixel down the detector and parallel to the axis of flow to avoid image streaking. For example, the instrument can operate at a continuous data rate of approximately 30 megapixels per second and integrate signal from each object for 10 milliseconds, which allows the detection of even faint fluorescent probes within cell images that are acquired at high speed. Attention to pump and fluidic system design to achieve highly laminar, non-pulsatile flow can eliminate cell rotation or lateral translation on the time scale of the imaging process (see, e.g., U.S. Pat. No. 6,532,061). Every pixel read from the CCD is analyzed by a real-time algorithm that detects the presence of object images and calculates a number of basic morphometric and photometric features, which can be used as criteria for data storage. Data files encompassing 10,000-20,000 cells can be about 100 MB in size, and are stored and analyzed using standard personal computers.

Example 6

Immunofluorescence Microscopy

Fixed control and treated cells were placed on a conventional glass slide (Erie Scientific, Portsmouth, N.H.), mixed 1:1 with Antifade (Molecular Probes) and covered with a cover slip. The cells were visualized at 400.times. using an Eclipse E600 (Nikon, Melville, N.Y.) fluorescence microscope equipped with filters appropriate for Alexa Fluor 488 (535/40 nm emission) and 7-AAD (630/60 nm emission).

Example 7

Conventional Analysis of Cells Induced to Undergo Apoptosis or Necrosis

Jurkat T cells were treated with peroxide (to induce necrosis), CPT (to induce apoptosis, which contained cells in both early and late stages of apoptosis), or were untreated (control). The three cell populations were then stained with Alexa Fluor 488 annexin V and 7-AAD and evaluated by brightfield, darkfield, and fluorescence microscopy, and by conventional flow cytometry (FIG. 2). The vast majority (>98%) of the control cells were viable at the time of staining, and were annexin V.sup.−, 7-AAD.sup.− (double negative, DN; FIG. 2A). CPT-treated (apoptotic) cells had two populations of cells, those that were annexin V.sup.+ (single positive, SP, or early apoptotic cells), and those that were annexin V.sup.+, 7-AAD.sup.+ (double positive, DP, or late apoptotic cells) (FIG. 2B). Similar to late apoptotic cells, peroxide-treated (necrotic cells) also stained positively with both annexin V and 7-AAD (FIG. 2C). However, the condensed, fragmented nuclei of late apoptotic cells could be easily distinguished from the intact nuclei of necrotic cells by immunofluorescence microscopy. In addition, apoptotic cells exhibited greater darkfield intensity and texture as compared to necrotic cells (see B and C image panels on right, respectively).

Example 8

Analysis of Heterogeneous Cell Population Normal, Apoptotic and Necrotic

A mixture of control, apoptotic, and necrotic Jurkat cells (individually prepared as described in Examples 1 and 2) were analyzed in parallel by conventional flow cytometry and on an ImageStream 100™ (Beta system, multispectral imaging flow cytometer). In this experiment, all cells were stained with Alexa Fluor 488-conjugated annexin V and 7-AAD. Necrotic cells were also stained with PE-conjugated anti-HLA class I before mixing the cell populations to aid in distinguishing necrotic cells from late stage apoptotic cells, and to permit "backgating" when necessary. On the ImageStream 100, each cell was simultaneously imaged in darkfield (488 nm laser side scatter), green fluorescence (500-550 nm, annexin V channel), orange fluorescence (550-600 nm, PE channel), red fluorescence (600-650 nm, 7-AAD channel), and brightfield (660-720 nm). Cells were grouped into live (DN), early apoptotic (SP), or double positive (DP, which would include late apoptotic and necrotic cells) populations based on the total intensities of annexin V and 7-AAD staining.

Figure 3B:
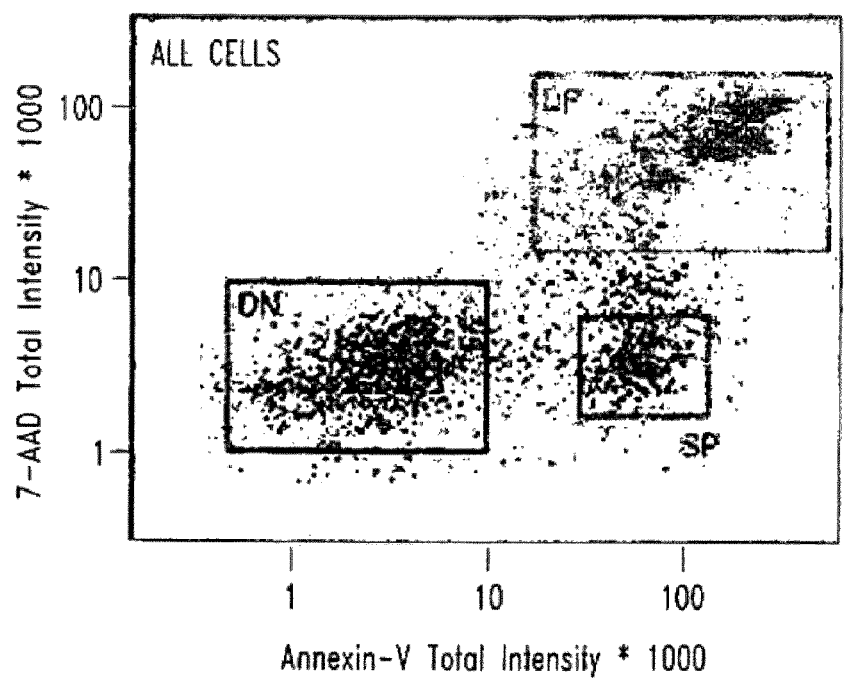
Figure 3C:
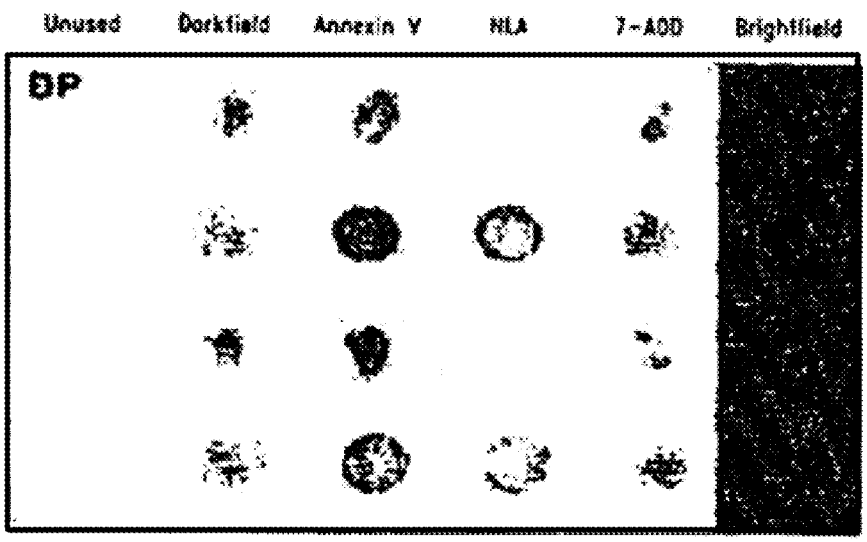
Figure 3D:
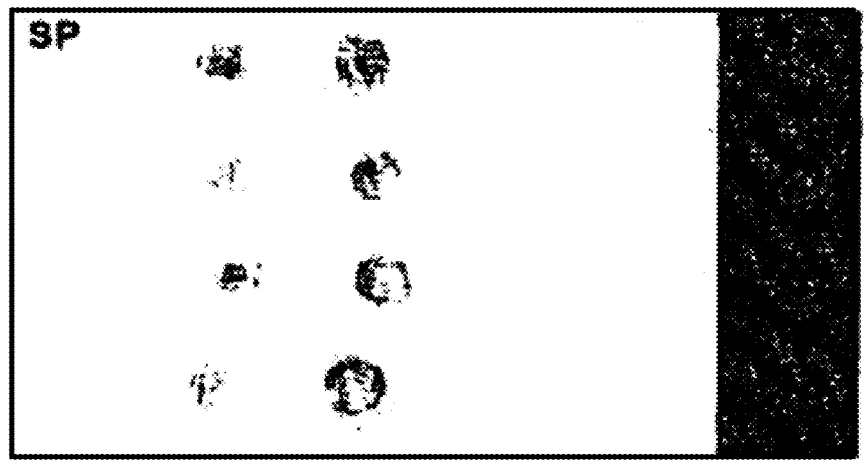
Figure 3E:
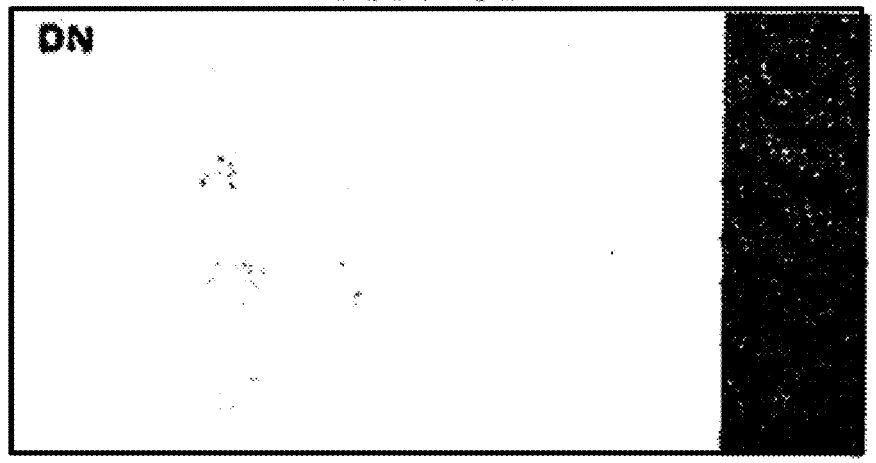

Similar bivariate dot-plots of annexin V and 7-AAD staining were obtained in analyses from both the conventional flow cytometer (see FIG. 3A) and the multispectral imaging flow cytometer (see FIG. 3B). However, a unique aspect of data collected on the ImageStream 100™ is that each data point can be "clicked on" to observe the cell imagery associated with each data point. Consequently, each population gate can be used to perform a "virtual cell sort" by displaying individual images of cells that fall within each gate—for example, representative images of cells contained in the DP, SP and DN gates can be "virtually sorted," as shown in FIGS. 3C, D and E, respectively, with each image row representing a different cell. Early apoptotic cells (cells in the SP gate) appear slightly shrunken, with more complex brightfield and darkfield morphologies, as compared to live cells in the DN gate. The double positive (DP) population contains cells with two distinct morphologies—one containing small, irregularly shaped cells with condensed, fragmented nuclei; and a second containing larger cells with large, unfragmented nuclei that stained uniformly with 7-AAD. The morphology of these two populations of cells is consistent with cells in the late stage of apoptosis and necrosis, respectively. Thus, in the absence of imagery provided by the multispectral imaging flow cytometer, data obtained from a conventional flow cytometer does not permit discrimination of similarly stained cells, such as late apoptotic cells from necrotic cells.

Example 9

Conventional Methods to Distinguish Late Apoptotic and Necrotic Cells

As noted in Example 8, although advanced apoptotic and necrotic cells differ morphologically, they cannot be distinguished based solely on annexin V and 7-AAD fluorescence. Plotting the mixed late apoptotic and necrotic DP population on a forward scatter vs. side scatter (FSC vs. SSC) plot reveals two distinct populations of cells (see FIG. 4A). Analysis of the DP population of cells obtained on the conventional flow cytometer for staining with PE (which was used to stain only the necrotic subpopulation of cells) permits separation of the necrotic and apoptotic subpopulations of cells (FIG. 4B). Backgating the PE positive necrotic population in blue reveals that the low SSC population consists of necrotic cells (FIG. 4C). However, without the aid of an extra marker (in this case, anti-HLA class I-PE) or imagery as described in Example 8, data obtained from a conventional flow cytometer does not permit discrimination of similarly stained cells, such as late apoptotic cells from necrotic cells.

Example 10

Multispectral Identification of Late Apoptotic and Necrotic Cells

Analysis of the DP population with IDEAS™ software for size (Brightfield Area) and Scatter Peak Intensity also revealed two populations of cells (FIG. 4D). The nuclei of cells that fell within the high brightfield area, low scatter peak intensity area (R3) were intact, uniformly stained with 7-AAD, and had a morphology consistent with necrotic cells. The nuclei of cells that fell within the low brightfield area, high scatter peak intensity area (R4) were condensed and fragmented, and had a morphology consistent with cells in the late stages of apoptosis. Backgating PE-positive cells (identified in the histogram shown in FIG. 4E) in yellow verified that R3 gated cells were derived from the necrotic treatment group (FIG. 4F). This conclusion is further supported by morphologic examination of cells in the image galleries of the R3 and R4 gated cells, and confirms that the low area/high texture cells were apoptotic (HLA-class I PE.sup.+ cells containing fragmented 7-AAD staining nuclei; lower right gallery) while high area/low texture cells were necrotic (HLA class I-PE.sup.+ cells containing uniform 7-AAD staining nuclei; upper right gallery). Thus, the data obtained from mulitspectral imaging is provided in form that allows one to distinguish similarly stained cells, such as late apoptotic cells from necrotic cells.

Example 11

Complex Morphologic Feature Identity Using Multispectral Imaging

Multispectral image data collection not only enables calculation of standard intensity-based parameters and statistics employed in conventional flow cytometry, but also permits quantitation of numerous other morphologic features (e.g., cell area, perimeter, aspect ratio, texture, spot counts, cell centroid, gradient intensity, spatial frequency). Using this capability, it is possible to distinguish all four cell populations (i.e., live, early apoptotic, late apoptotic and necrotic cells) in a single step using morphologic features derived from 7-AAD, brightfield and darkfield imagery (and in the absence of other staining procedures often used) to "identify" apoptotic cells.

By subtracting the 7-AAD image area (nuclear size) from the Brightfield area (cell size), a value is obtained that is an indication of cytoplasmic size. When this complex morphologic feature (herein referred to as "Brightfield 7-AAD Area") was used in conjunction with a feature derived from darkfield imagery (i.e., 488 nm spatial scatter frequency, which is an indication of internal cell complexity or cell granularity), four subpopulations of cells became evident (see FIG. 5). The 488 nm spatial scatter frequency can be calculated by computing the standard deviation of the individual pixel intensities within the segmented dark field image mask.

Live cells (depicted in blue, FIG. 5, center panel) excluded the cell-impermeant 7-AAD fluorescent DNA binding dye, which minimized the nuclear image area and resulted in cells with a large calculated cytoplasmic area.

Early apoptotic cells (depicted in green, FIG. 5, center panel) are just as effective as live cells at excluding 7-AAD, but their total brightfield area is slightly smaller due to the early stages of cytoplasmic blebbing, thereby resulting in an intermediate value for the "Brightfield-7AAD Area" parameter. Also associated with the early stages of apoptosis is a significant increase in 488 nm scatter peak intensity, which clearly separates these cells from live cells on the vertical axis of the dot-plot. Again, it should be understood that while color Figures have not been provided, the different cell populations (live, early apoptotic, late apoptotic, and necrotic) are displayed in different colors in the IDEAS™ software.

Necrotic cells (depicted in yellow, FIG. 5, center panel) and late apoptotic cells (depicted in red, FIG. 5, center panel) both had compromised membrane integrity, which permits free entry of 7-AAD and thus strong nuclear images of relatively large area, shifting these populations to the left on the dot-plot. However, these two cell populations can be clearly separated based on the peak intensity measurements derived from their 488 nm scatter parameters. Necrotic cells produce darkfield images of relatively low complexity compared to the more complex and heterogeneous darkfield images of late apoptotic cells, thus clearly separating the two populations in the vertical axis. Again, it should be understood that while color Figures have not been provided, the different cell populations (live, early apoptotic, late apoptotic, and necrotic) are displayed in different colors in the IDEAS™ software.

Inspection of the associated image galleries associated with these four gated populations of cells confirmed the classification of each population (see FIG. 5, upper and lower panels).

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for classifying a specific cell as one of the following four types of cells, a viable cell, a necrotic cell, an early apoptotic cell in which a cellular membrane of the cell is still intact, and a late apoptotic cell in which the cellular membrane of the cell is not intact, using only a single nuclear marker and image data from the cell, the method comprising the steps of:
    (a) exposing the specific cell to only a single nuclear marker that will bind to DNA in a nucleus of the specific cell in the event that the cellular membrane of the specific cell is not intact;
    (b) collecting image data from the specific cell, the image data comprising:
        (i) a darkfield image of the specific cell, the darkfield image corresponding to a side scatter image of the specific cell;
        (ii) a brightfield image of the specific cell; and
        (iii) a fluorescent image of the specific cell, the fluorescent image enabling the location of the single nuclear marker in the specific cell to be determined;
    (c) using the brightfield image of the specific cell and the fluorescent image of the specific cell to calculate a cytoplasmic size of the specific cell;
    (d) analyzing the fluorescent image of the specific cell to determine if the nuclear marker is present in the nucleus of the specific cell;
    (e) using the darkfield image of the specific cell to calculate a spatial scatter frequency metric indicative of a granularity of the specific cell; and
    (f) classifying the specific cell as one of the four types of cells based on the following:
        (i) the cytoplasmic size of the specific cell;
        (ii) the darkfield scatter frequency metric of the specific cell; and
        (iii) the presence of the nuclear marker in the nucleus of the specific cell.

2. The method of claim 1, wherein the step of classifying the specific cell as one of the four types of cells comprises the step of classifying the specific cell as a viable cell when:
    (a) the cytoplasmic size of the specific cell is larger than a cytoplasmic size of a cell known to be an early apoptotic cell in which a cellular membrane of the cell is still intact;
    (b) the darkfield scatter frequency metric of the specific cell is smaller than a darkfield scatter frequency metric of a cell known to be an early apoptotic cell in which a cellular membrane of the cell is still intact; and
    (c) the nuclear marker is not present in the nucleus of the specific cell.

3. The method of claim 1, wherein the step of classifying the specific cell as one of the four types of cells comprises the step of classifying the specific cell as a viable cell when:
   (a) the cytoplasmic size of the specific cell is larger than a cytoplasmic size of a cell known to be an early apoptotic cell in which a cellular membrane of the cell is still intact; and
   (b) the nuclear marker is not present in the nucleus of the specific cell.

4. The method of claim 1, wherein the step of classifying the specific cell as one of the four types of cells comprises the step of classifying the specific cell as a viable cell when:
   (a) the darkfield scatter frequency metric of the specific cell is smaller than a darkfield scatter frequency metric of a cell known to be an early apoptotic cell in which a cellular membrane of the cell is still intact; and
   (b) the nuclear marker is not present in the nucleus of the specific cell.

5. The method of claim 1, wherein the step of classifying the specific cell as one of the four types of cells comprises the step of classifying the specific cell as an early apoptotic cell in which a cellular membrane of the cell is still intact when:
   (a) the cytoplasmic size of the specific cell is smaller than a cytoplasmic size of a cell known to be a viable cell in which a cellular membrane of the cell is still intact;
   (b) the darkfield scatter frequency metric of the specific cell is larger than a darkfield scatter frequency metric of a cell known to be a viable cell in which a cellular membrane of the cell is still intact; and
   (c) the nuclear marker is not present in the nucleus of the specific cell.

6. The method of claim 1, wherein the step of classifying the specific cell as one of the four types of cells comprises the step of classifying the specific cell as an early apoptotic cell in which a cellular membrane of the cell is still intact when:
   (a) the cytoplasmic size of the specific cell is smaller than a cytoplasmic size of a cell known to be a viable cell in which a cellular membrane of the cell is still intact; and
   (b) the nuclear marker is not present in the nucleus of the specific cell.

7. The method of claim 1, wherein the step of classifying the specific cell as one of the four types of cells comprises the step of classifying the specific cell as a late apoptotic cell in which a cellular membrane of the cell is not intact when:
   (a) the darkfield scatter frequency metric of the specific cell is larger than a darkfield scatter frequency metric of a cell known to be a necrotic cell; and
   (b) the nuclear marker is present in the nucleus of the specific cell.

8. The method of claim 1, wherein the step of classifying the specific cell as one of the four types of cells comprises the step of classifying the specific cell as a necrotic cell when:
   (a) the darkfield scatter frequency metric of the specific cell is smaller than a darkfield scatter frequency metric of a cell known to be a late apoptotic cell; and
   (b) the nuclear marker is present in the nucleus of the specific cell.

9. The method of claim 1, wherein the single nuclear marker is 7-aminoactinomycin D.

10. A method for classifying a specific cell as one of the following four types of cells, a viable cell, a necrotic cell, an early apoptotic cell in which a cellular membrane of the cell is still intact, and a late apoptotic cell in which the cellular membrane of the cell is not intact, using only a single nuclear marker and image data from the cell, the method comprising the steps of:
   (a) exposing the specific cell to only a single nuclear marker that will bind to DNA in a nucleus of the specific cell in the event that the cellular membrane of the specific cell is not intact;
   (b) collecting image data from the specific cell, the image data comprising:
      (i) a darkfield image of the specific cell, the darkfield image corresponding to a side scatter image of the specific cell; and
      (ii) a fluorescent image of the specific cell, the fluorescent image enabling the location of the single nuclear marker in the specific cell to be determined;
   (c) analyzing the fluorescent image of the specific cell to determine if the nuclear marker is present in the nucleus of the specific cell;
   (d) using the darkfield image of the specific cell to calculate a spatial scatter frequency metric indicative of a granularity of the specific cell;
   (e) classifying the specific cell as being a viable cell when:
      (i) the nuclear marker is not present in the nucleus of the specific cell; and
      (ii) the darkfield scatter frequency metric of the specific cell is smaller than a darkfield scatter frequency metric of a cell known to be an early apoptotic cell in which a cellular membrane of the cell is still intact;
   (f) classifying the specific cell as being an early apoptotic cell when:
      (i) the nuclear marker is not present in the nucleus of the specific cell; and
      (ii) the darkfield scatter frequency metric of the specific cell is larger than a darkfield scatter frequency metric of a cell known to be a viable cell;
   (g) classifying the specific cell as being a late apoptotic cell when:
      (i) the nuclear marker is present in the nucleus of the specific cell; and
      (ii) the darkfield scatter frequency metric of the specific cell is larger than a darkfield scatter frequency metric of a cell known to be a necrotic cell; and
   (h) classifying the specific cell as being a necrotic cell when:
      (i) the nuclear marker is present in the nucleus of the specific cell; and
      (ii) the darkfield scatter frequency metric of the specific cell is smaller than a darkfield scatter frequency metric of a cell known to be a late apoptotic cell.

11. The method of claim 10, wherein the single nuclear marker is 7-aminoactinomycin D.

12. A method for classifying a population of biological cells into four different types of cells, the four types of cells consisting of viable cells, necrotic cells, early apoptotic cells in which a cellular membrane of the cell is still intact, and late apoptotic cells in which the cellular membrane of the cell is not intact, using only a single nuclear marker and image data acquired from each cell in the population of cells, the method comprising the steps of:
   (a) exposing each cell in the population of cells to only one nuclear marker that will bind to DNA in a nucleus of the cell in the event that the cellular membrane of the cell is not intact;
   (b) collecting image data from each cell in the population of cells, the image data for each cell comprising:
      (i) a darkfield image of the cell, the darkfield image corresponding to a side scatter image of the cell;
      (ii) a brightfield image of the cell;

(iii) a fluorescent image of the cell, the fluorescent image enabling the location of the nuclear marker in the cell to be determined;

(c) for each specific cell in the population of cells, using the brightfield image of the specific cell and the fluorescent image of the specific cell to calculate a cytoplasmic size of the specific cell;

(d) for each specific cell in the population of cells, using the darkfield image of the specific cell to calculate a spatial scatter frequency metric indicative of a granularity of the specific cell;

(e) generating a dot plot where data from each cell in the population of cells is displayed, the dot plot being generated using the cytoplasmic size of each cell as a first axis of the dot plot, and the spatial scatter frequency metric of the darkfield image of each cell as a second axis of the dot plot; and (f) using the dot plot to classify the population of cells into the four different types of cells based on the relative location of each cell in the dot.

13. The method of claim 12, wherein the single nuclear marker is 7-aminoactinomycin D.

14. The method of claim 12, wherein the step of generating the dot plot comprises the step of displaying each viable cell on the dot plot at a first portion of the dot plot corresponding to cells having a relatively larger cytoplasmic size and a relatively lower darkfield scatter frequency metric.

15. The method of claim 14, wherein the first portion of the dot plot corresponds to a lower left quadrant of the dot plot.

16. The method of claim 12, wherein the step of generating the dot plot comprises the step of displaying each early apoptotic on the dot plot at a second portion of the dot plot corresponding to cells having a relatively larger cytoplasmic size and a relatively higher darkfield scatter frequency metric.

17. The method of claim 16, wherein the second portion of the dot plot corresponds to an upper left quadrant of the dot plot.

18. The method of claim 12, wherein the step of generating the dot plot comprises the step of displaying each necrotic cell on the dot plot at a third portion of the dot plot corresponding to cells having a relatively smaller cytoplasmic size and a relatively lower darkfield scatter frequency metric.

19. The method of claim 18, wherein the third portion of the dot plot corresponds to a lower right quadrant of the dot plot.

20. The method of claim 12, wherein the step of generating the dot plot comprises the step of displaying each late apoptotic cell on the dot plot at a fourth portion of the dot plot corresponding to cells having a relatively smaller cytoplasmic size and a relatively higher darkfield scatter frequency metric, the fourth portion of the dot plot corresponding to an upper right quadrant of the dot plot.

* * * * *